(12) United States Patent
Milliman et al.

(10) Patent No.: US 8,317,073 B2
(45) Date of Patent: Nov. 27, 2012

(54) SURGICAL INSTRUMENT WITH INDICATOR

(75) Inventors: Keith L. Milliman, Bethel, CT (US);
Thomas R. Hessler, Bethel, CT (US);
Stephen R. Paul, E. Hartford, CT (US);
Thomas Wenchell, Durham, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/397,794

(22) Filed: Feb. 16, 2012

(65) Prior Publication Data

US 2012/0145766 A1 Jun. 14, 2012

Related U.S. Application Data

(63) Continuation of application No. 12/697,519, filed on Feb. 1, 2010, now Pat. No. 8,132,703, which is a continuation of application No. 12/544,479, filed on Aug. 20, 2009, now abandoned.

(60) Provisional application No. 61/093,753, filed on Sep. 3, 2008.

(51) Int. Cl.
*A61B 17/068* (2006.01)
(52) U.S. Cl. ............ 227/175.1; 227/19; 227/175.2
(58) Field of Classification Search ............ 227/19, 227/175.2, 175.1, 176.1, 180.1, 181.1
See application file for complete search history.

(56) References Cited

U.S. PATENT DOCUMENTS

| | | |
|---|---|---|
| 4,379,457 A | 4/1983 | Gravener et al. |
| 4,527,724 A | 7/1985 | Chow et al. |
| 4,892,244 A | 1/1990 | Fox et al. |
| 5,005,749 A | 4/1991 | Aranyi |
| 5,071,052 A | 12/1991 | Rodak et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,333,773 A | 8/1994 | Main et al. |
| 5,350,104 A | 9/1994 | Main et al. |
| 5,403,312 A | 4/1995 | Yates et al. |
| 5,443,198 A | 8/1995 | Viola et al. |
| 5,474,223 A | 12/1995 | Viola et al. |
| 5,529,235 A | 6/1996 | Boiarski et al. |
| 5,533,661 A | 7/1996 | Main et al. |
| 5,535,935 A | 7/1996 | Vidal et al. |
| 5,535,937 A | 7/1996 | Boiarski et al. |
| 5,607,436 A | 3/1997 | Pratt et al. |
| 5,685,474 A | 11/1997 | Seeber |
| 5,688,270 A | 11/1997 | Yates et al. |
| 5,697,543 A | 12/1997 | Burdorff |
| 5,709,680 A | 1/1998 | Yates et al. |

(Continued)

FOREIGN PATENT DOCUMENTS

EP 0639349 2/1995

(Continued)

*Primary Examiner* — Scott A. Smith

(57) ABSTRACT

A surgical stapling instrument including a handle assembly, an elongated body portion extending distally from the handle assembly, and a head portion. The handle assembly includes a firing trigger and a firing indicator. The firing trigger is movable between a first non-actuated position and a second actuated position. The head portion is disposed adjacent a distal portion of the elongated body portion and includes an anvil assembly and a shell assembly. The anvil assembly is movable in relation to the shell assembly between spaced and approximated positions. Engagement structure of the firing trigger moves the firing indicator from a first position to a second position when the firing trigger is moved from its first non-actuated position toward its second actuated position.

17 Claims, 9 Drawing Sheets

U.S. PATENT DOCUMENTS

| | | | |
|---|---|---|---|
| 5,762,255 A | 6/1998 | Chrisman et al. |
| 5,797,537 A | 8/1998 | Oberlin et al. |
| 5,799,857 A | 9/1998 | Robertson et al. |
| 5,807,393 A | 9/1998 | Williamson, IV et al. |
| 5,810,811 A | 9/1998 | Yates et al. |
| 5,820,009 A | 10/1998 | Melling et al. |
| 5,833,690 A | 11/1998 | Yates et al. |
| 5,882,340 A | 3/1999 | Yoon |
| 5,915,616 A | 6/1999 | Viola et al. |
| 6,010,054 A | 1/2000 | Johnson et al. |
| 6,024,741 A | 2/2000 | Williamson, IV et al. |
| 6,050,472 A | 4/2000 | Shibata |
| 6,066,145 A | 5/2000 | Wurster |
| H1904 H | 10/2000 | Yates et al. |
| 6,269,997 B1 | 8/2001 | Balazs et al. |
| 6,601,748 B1 | 8/2003 | Fung et al. |
| 6,769,594 B2 | 8/2004 | Orban, III |
| 6,945,444 B2 | 9/2005 | Gresham et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,234,624 B2 | 6/2007 | Gresham et al. |
| 7,237,708 B1 | 7/2007 | Guy et al. |
| 7,303,106 B2 | 12/2007 | Milliman et al. |
| 7,364,060 B2 | 4/2008 | Milliman |
| 7,556,186 B2 | 7/2009 | Milliman |
| 7,784,663 B2 | 8/2010 | Shelton, IV |
| 7,866,527 B2 | 1/2011 | Hall et al. |
| 7,886,951 B2 | 2/2011 | Hessler |
| 8,132,703 B2 * | 3/2012 | Milliman et al. ......... 227/175.1 |
| 2005/0006432 A1 | 1/2005 | Racenet et al. |
| 2005/0006433 A1 | 1/2005 | Milliman et al. |
| 2005/0067457 A1 | 3/2005 | Shelton, IV et al. |
| 2005/0067458 A1 | 3/2005 | Swayze et al. |
| 2005/0103819 A1 | 5/2005 | Racenet et al. |
| 2005/0116009 A1 | 6/2005 | Milliman |
| 2005/0205640 A1 | 9/2005 | Milliman |
| 2006/0025816 A1 | 2/2006 | Shelton, IV |
| 2006/0097025 A1 | 5/2006 | Milliman et al. |
| 2006/0175375 A1 | 8/2006 | Shelton, IV et al. |
| 2006/0201992 A1 | 9/2006 | Racenet et al. |
| 2006/0212069 A1 | 9/2006 | Shelton, IV |
| 2006/0219752 A1 | 10/2006 | Arad et al. |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0273135 A1 | 12/2006 | Beetel |
| 2006/0278680 A1 | 12/2006 | Viola et al. |
| 2007/0034670 A1 | 2/2007 | Racenet et al. |
| 2007/0060952 A1 | 3/2007 | Roby et al. |
| 2007/0075117 A1 | 4/2007 | Milliman et al. |
| 2007/0108252 A1 | 5/2007 | Racenet et al. |
| 2007/0175964 A1 | 8/2007 | Shelton, IV et al. |
| 2008/0142566 A1 | 6/2008 | Gresham et al. |
| 2008/0312687 A1 | 12/2008 | Blier |

FOREIGN PATENT DOCUMENTS

| | | |
|---|---|---|
| EP | 1997438 | 12/2008 |
| EP | 2090255 | 8/2009 |

* cited by examiner

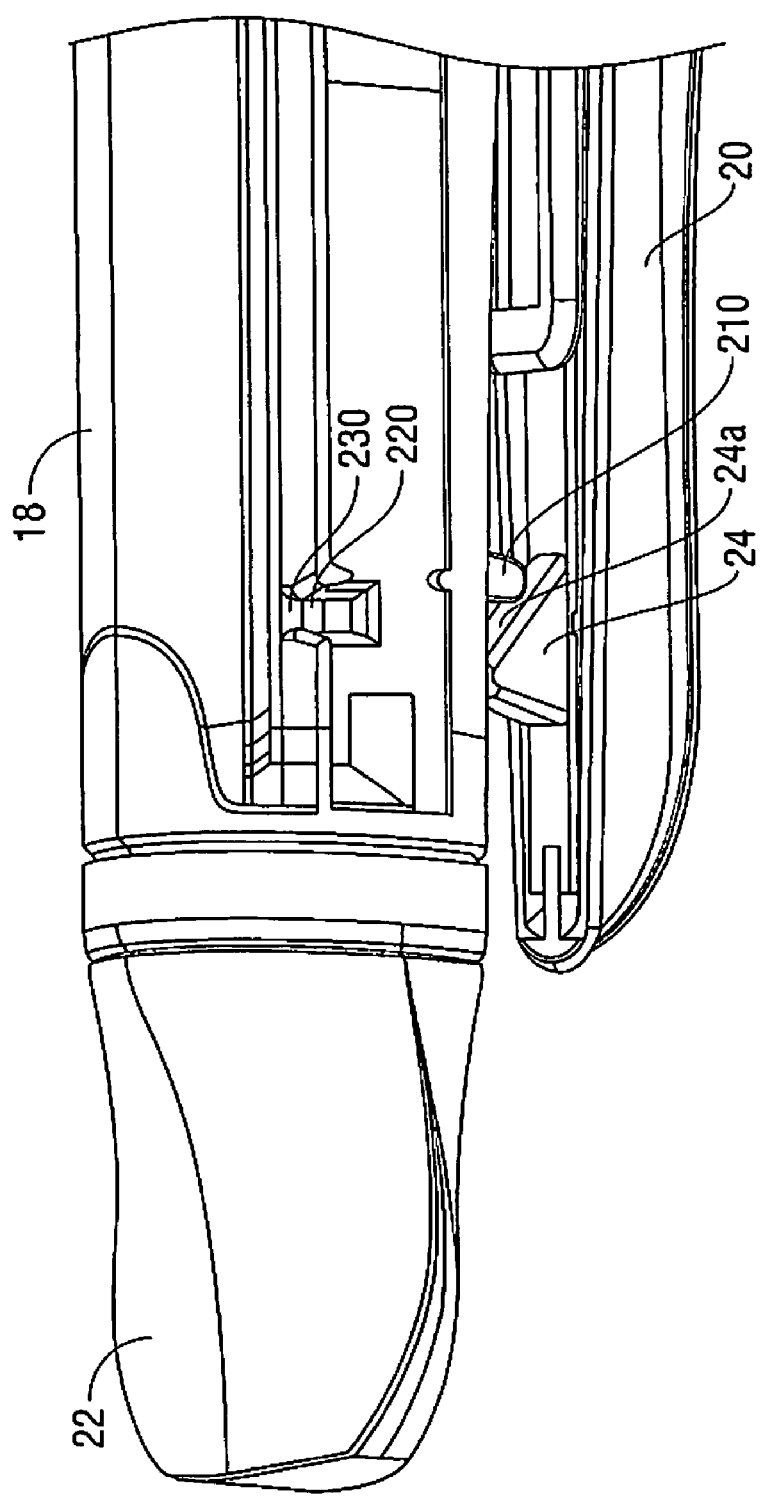

SURGICAL INSTRUMENT WITH INDICATOR

This application is a continuation of U.S. application Ser. No. 12/697,519, filed on Feb. 1, 2010, now U.S. Pat. No. 8,132,703, which is a continuation of U.S. application Ser. No. 12/544,479, filed Aug. 20, 2009, now abandoned, which claims priority from provisional patent application Ser. No. 61/093,753, filed Sep. 3, 2008. The entire contents of each of these applications are incorporated herein by reference.

BACKGROUND

1. Technical Field

The present disclosure relates generally to a surgical stapling instrument for applying surgical staples to body tissue. More particularly, the present disclosure relates to a surgical stapling instrument suitable with a firing indicator.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described for example in U.S. Pat. Nos. 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component as these components are approximated. The clamped tissue is stapled by driving one or more staples from the staple holding component so that the ends of the staples pass through the tissue and are deformed by the anvil head. An annular knife is concurrently advanced to core tissue within the hollow organ to free a tubular passage within the organ.

Besides anastomosis of hollow organs, surgical stapling instruments for performing circular anastomosis have been used to treat internal hemorrhoids in the rectum. Typically, during use of a circular stapling instrument for hemorrhoid treatment, the anvil head and the staple holding component of the surgical stapling instrument are inserted through the anus and into the rectum with the anvil head and the staple holding component in an open or unapproximated position. Thereafter, a pursestring suture is used to pull the internal hemorrhoidal tissue towards the anvil rod. Next, the anvil head and the staple holding component are approximated to clamp the hemorrhoid tissue between the anvil head and the staple holding component. The stapling instrument is fired to remove the hemorrhoidal tissue and staple the cut tissue. In stapled hemorrhoidopexy, a strip of mucosa and submucosa at the top of the hemorrhoids is removed by the stapling instrument, thereby treating the hemorrhoids by inhibiting blood flow to the tissue.

In certain situations, it is desirable to provide an indication to the user regarding the firing status of the instrument. Accordingly, it would be desirable for a surgical instrument to include an indicator to let the user know when the instrument has been fired.

SUMMARY

The present disclosure relates to a surgical stapling instrument including a handle assembly, an elongated body portion extending distally from the handle assembly, and a head portion. The handle assembly includes a firing trigger and a firing indicator. The firing trigger is movable between a first non-actuated position and a second actuated position. The head portion is disposed adjacent a distal portion of the elongated body portion and includes an anvil assembly and a shell assembly. The anvil assembly is movable in relation to the shell assembly between spaced and approximated positions. Engagement structure of the firing trigger moves the firing indicator from a first position to a second position when the firing trigger is moved from its first non-actuated position toward its second actuated position.

In a preferred embodiment the firing indicator is rotatable with respect to a stationary handle of the handle assembly and includes a pawl engaged by the firing trigger when moved from its first non-actuated position toward its second actuated position. In a preferred embodiment, the engagement structure of the firing trigger includes a tab extending toward the stationary handle. The tab can be angled with respect to the longitudinal axis defined by the firing trigger.

The firing indicator preferably includes indicia thereon wherein the indicia is visible to the user when the firing indicator is in its second position.

The present disclosure also relates to a surgical stapling instrument including a handle assembly, an elongated body portion, a head portion, an approximation indicator and a firing indicator. The handle assembly includes a firing trigger. The firing trigger is movable between a first non-actuated position and a second actuated position. The elongated body portion extends distally from the handle assembly. The head portion is disposed adjacent a distal portion of the elongated body portion and includes an anvil assembly and a shell assembly. The anvil assembly is movable in relation to the shell assembly between spaced and approximated positions. The approximation indicator is disposed in mechanical cooperation with the handle assembly and is configured to move from a first position towards a second position in response to the anvil assembly moving in relation to the shell assembly towards its approximated position. The firing indicator is disposed in mechanical cooperation with the handle assembly and is configured to move from a first position towards a second position in response to the firing trigger moving towards its second actuated position.

In a preferred embodiment the firing indicator is rotatable with respect to a stationary handle of the handle assembly and includes a pawl engaged by the firing trigger when moved from its first non-actuated position toward its second actuated position. In a preferred embodiment, the engagement structure of the firing trigger includes a tab extending toward the stationary handle. The tab can be angled with respect to the longitudinal axis defined by the firing trigger.

DESCRIPTION OF THE DRAWINGS

Various embodiments of the presently disclosed surgical stapling instrument are disclosed herein with reference to the drawings, wherein:

FIG. 5 is a perspective view of the handle assembly of the surgical stapling instrument in the fired position of FIG. 3;

DETAILED DESCRIPTION OF EMBODIMENTS

Figure 1:
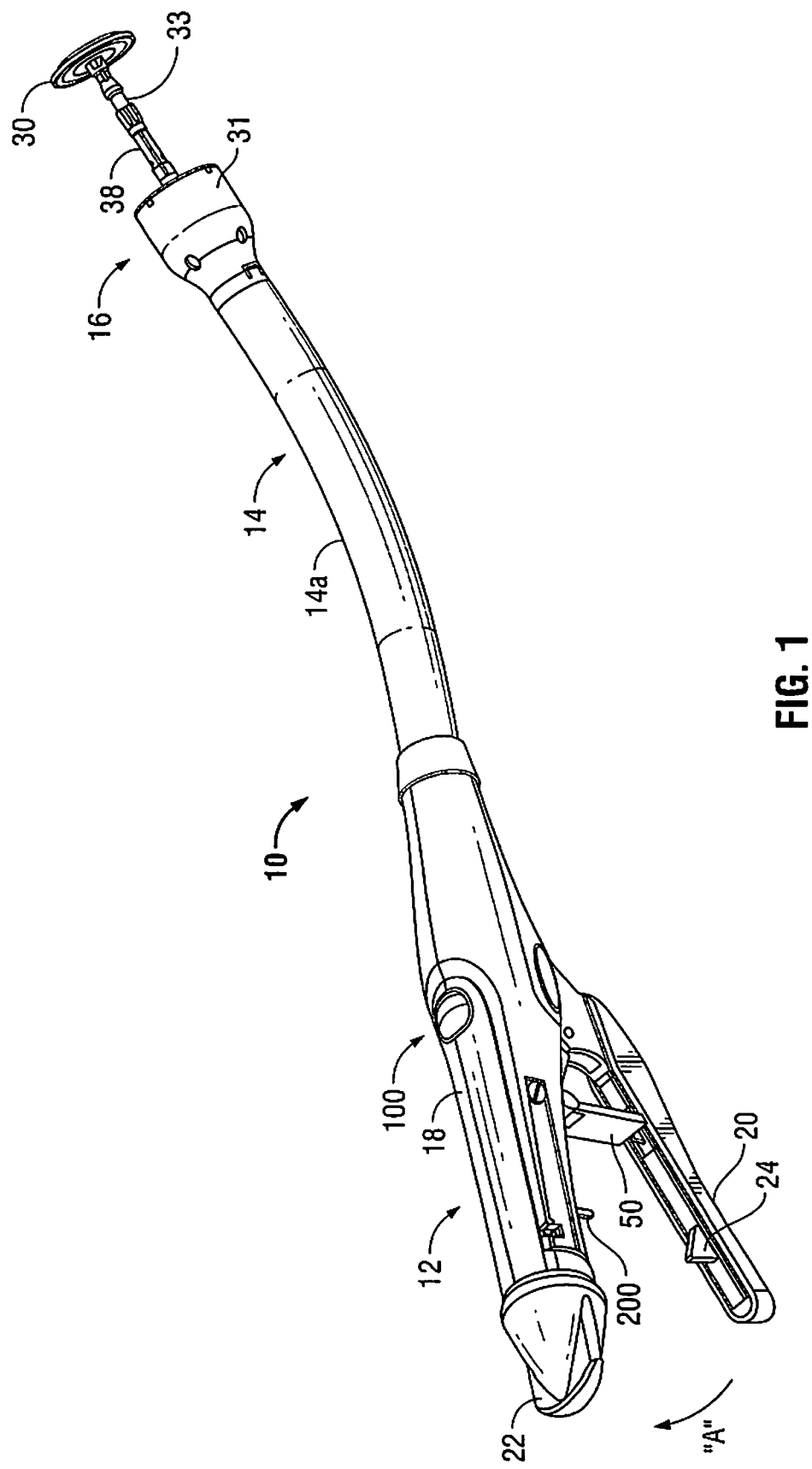
FIG. 1 is a perspective view of the presently disclosed surgical stapling instrument illustrated in an unapproximated position, in accordance with an embodiment of the present disclosure.

Embodiments of the presently disclosed surgical stapling instrument will now be described in detail with reference to the drawings in which like reference numerals designate identical or corresponding elements in each of the several views.

Throughout this description, the term "proximal" will refer to the portion of the instrument closer to the operator and the term "distal" will refer to the portion of the instrument further from the operator.

Figure 2:
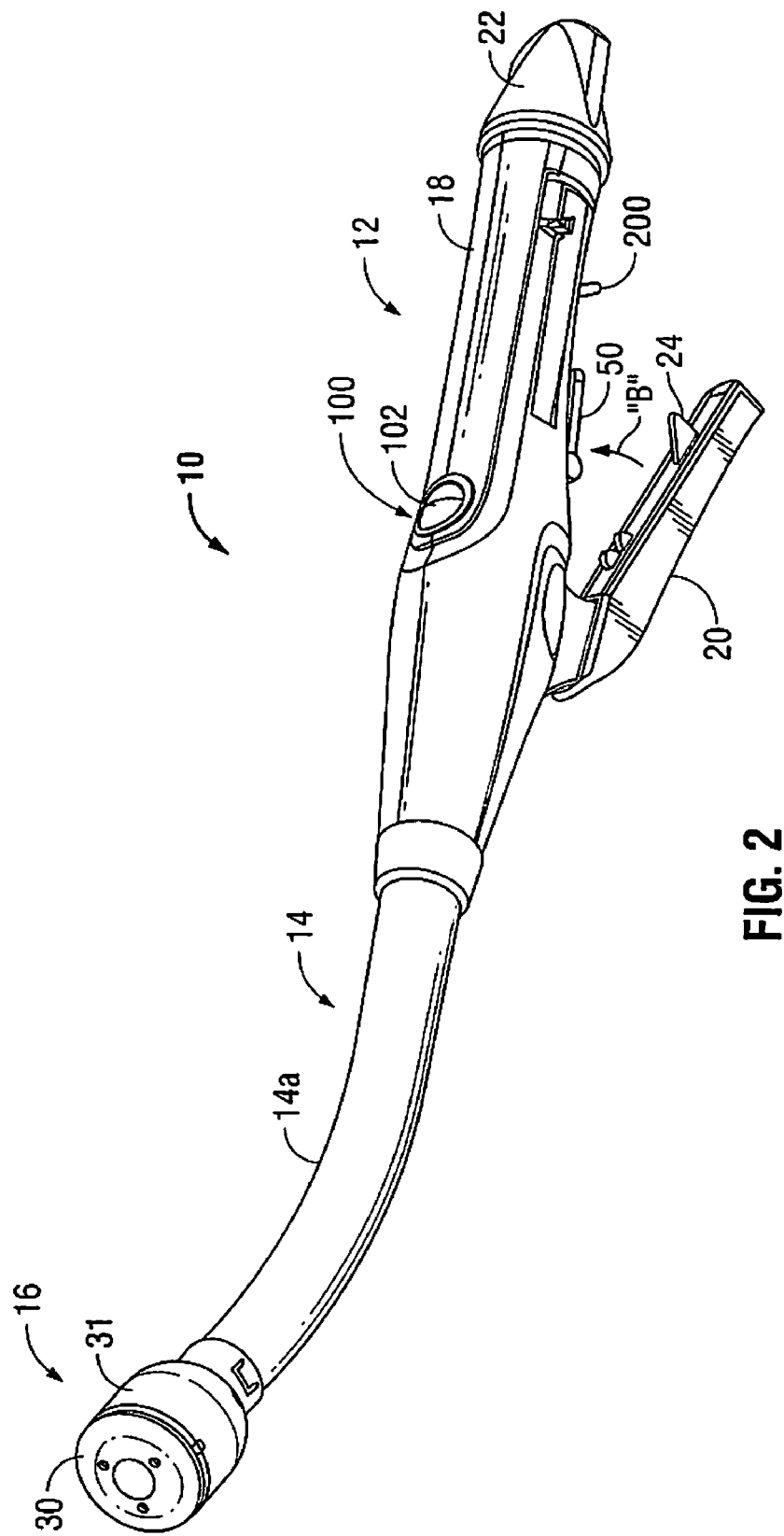
FIG. 2 is a perspective view of the surgical stapling instrument of FIG. 1 illustrated in an approximated unfired position.
Figure 3:
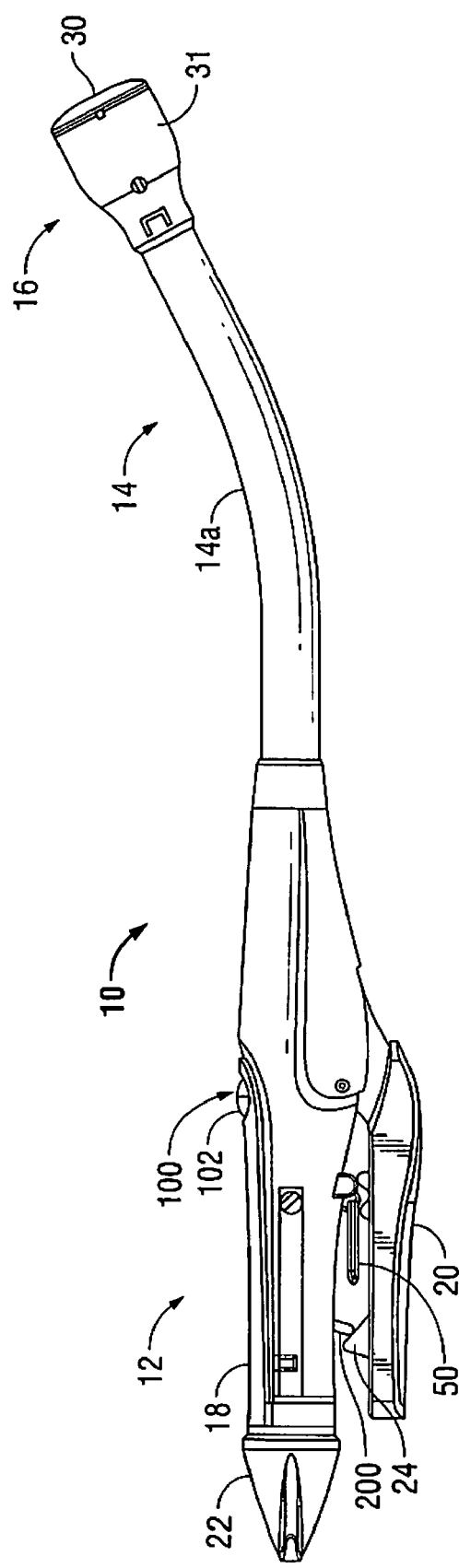
FIG. 3 is a perspective view of the surgical stapling instrument of FIG. 1 illustrated in a fired position.

FIGS. 1-3 illustrate one embodiment of the presently disclosed surgical stapling instrument shown generally as reference numeral 10. Briefly, surgical stapling instrument 10 includes a handle assembly 12, an elongated body portion 14 including a curved elongated outer tube 14a, and a head portion 16. Alternately, in some surgical procedures, e.g., the treatment of hemorrhoids, it is desirable to have a substantially straight body portion. The length, shape and/or the diameter of body portion 14 and head portion 16 may also be varied to suit a particular surgical procedure.

With continued reference to FIGS. 1-3, handle assembly 12 includes a stationary handle 18, a firing trigger 20, a rotatable approximation knob 22, an approximation indicator mechanism 100 and a firing indicator 200. Head portion 16 includes an anvil assembly 30 and a shell assembly 31. Anvil assembly 30 is movable in relation to shell assembly 31 between spaced and approximated positions.

Still referring to FIGS. 1-3, in operation, rotation of approximation knob 22 causes movement of anvil assembly 30 in relation to shell assembly 31 between spaced (FIG. 1) and approximated positions (FIGS. 2-3), as approximation knob 22 is operatively associated with anvil retainer 38 (FIG. 1), which is connected to anvil shaft or center rod 33 of anvil assembly 30. Rotation of approximation knob 22 in a first direction (e.g., clockwise) causes proximal movement of anvil assembly 30 by retracting anvil retainer 38, and rotation of approximation knob 22 in a second opposite direction (i.e., counter-clockwise) causes distal movement of anvil assembly 30 as anvil retainer 38 is advanced distally. Other approximation mechanisms are also contemplated.

Figure 4A:
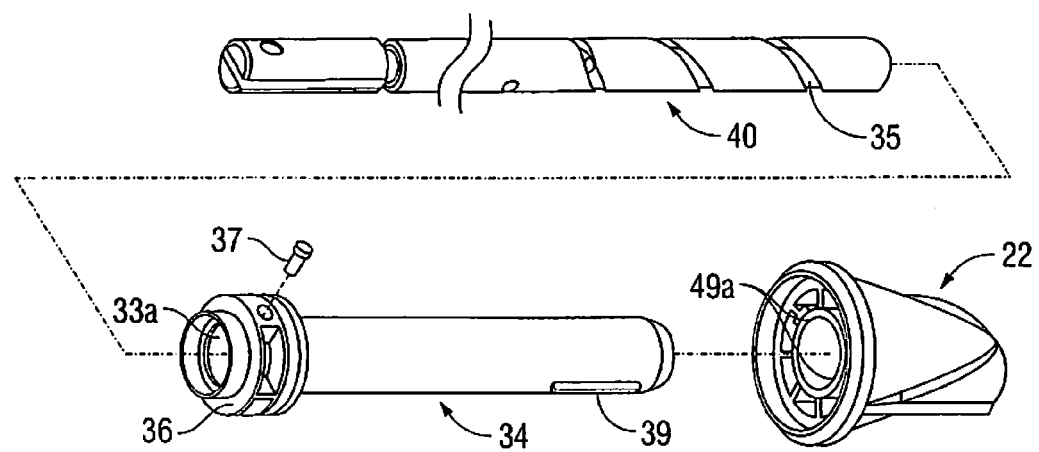
FIG. 4A is an exploded view of a portion of the approximation mechanism.
Figure 4B:
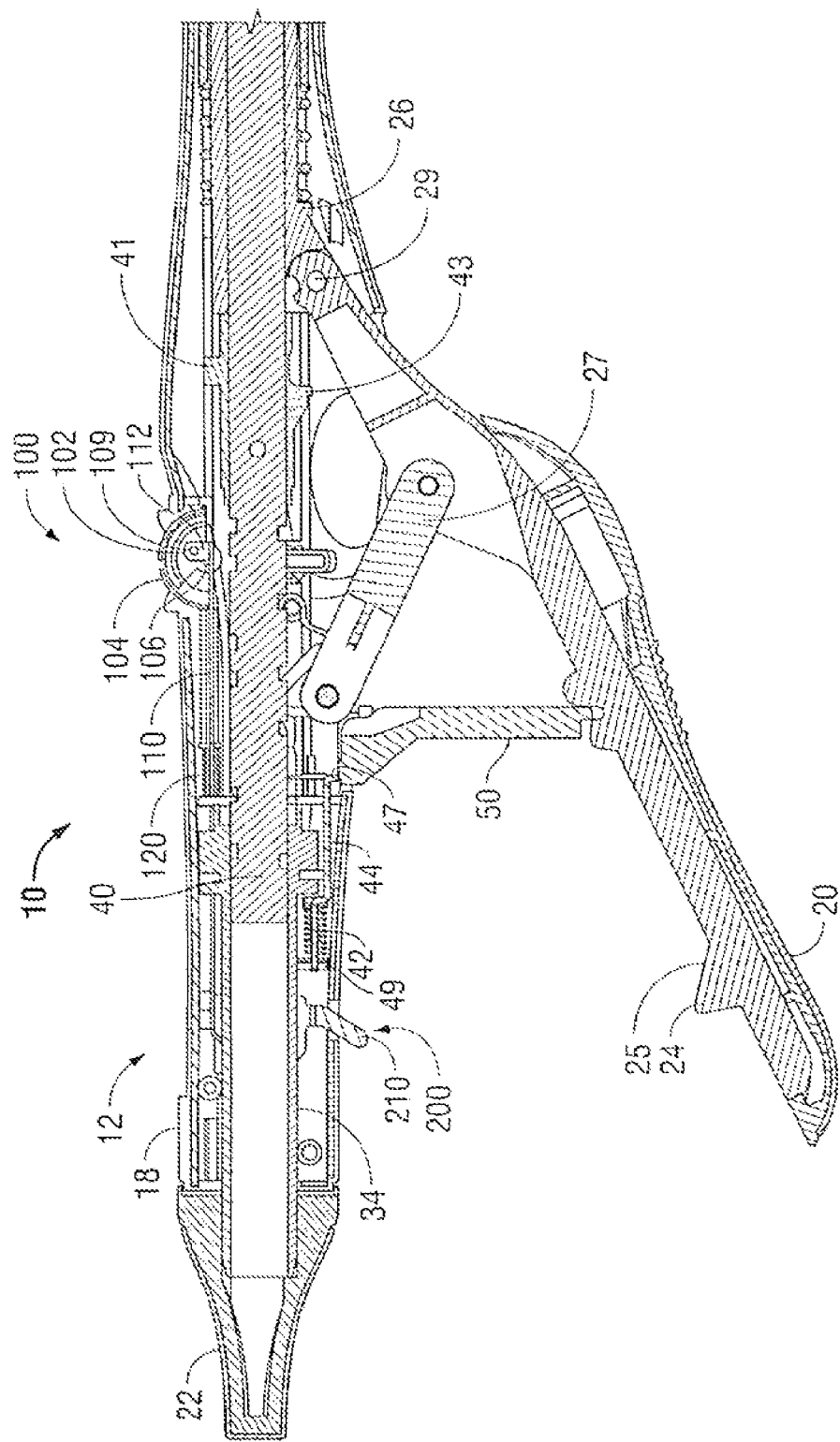
FIG. 4B is a longitudinal, cross-sectional view of a portion of the surgical instrument in the unapproximated position, as illustrated in FIG. 1.

More specifically, referring to FIGS. 4A and 4B, approximation knob 22 is mechanically engaged with a screw 40 and the screw 40 is in mechanical cooperation with anvil retainer 38 which is engaged with anvil assembly 30. As shown in FIG. 4A, the proximal portion of screw 40 has a helical channel 35 and is slidably positioned within central bore 33a of rotatable sleeve 34. The proximal portion of sleeve 34 extends through an opening in the proximal end of the stationary handle 18 and elongated ribs 39 on its outer surface are received in internal slots 49a of rotation knob 22 to fix sleeve 34 to knob 22. A pin 37 extends through cylindrical collar 36 of sleeve 34 into helical channel 35. Since sleeve 33 is axially fixed with respect to stationary handle 18, rotation of sleeve 34 about screw 40 causes pin 37 to move along channel 35 of screw 40 to effect axial movement of screw 40. Further details of the approximation mechanism are described in U.S. Pat. No. 7,303,106, the entire contents of which are incorporated herein by reference. Rotation of approximation knob 22 in the first direction causes the screw stop 40 to move proximally, which in turn causes proximal movement of anvil retainer 38 to approximate the attached anvil toward the fasteners.

Additionally, FIGS. 1-4 show a lockout mechanism including a trigger lock 50. Trigger lock 50 is disposed in mechanical cooperation with handle assembly 12 and maintains firing trigger 20 in an open inactivated position until anvil assembly 30 and shell assembly 31 have been approximated. With the trigger lock 50 in the blocking position shown in FIGS. 1 and 4B, wherein the anvil is in an unapproximated position, firing trigger 20 cannot be squeezed. As can be appreciated, the lockout mechanism therefore helps prevent staples from being fired prematurely, i.e. before approximation of the anvil assembly, by blocking movement of the firing trigger 20.

When the rotation knob 22 is rotated to approximate the anvil assembly 30, screw 40 and screw stop 40 move proximally, and a downwardly extending tab portion 43 of the screw stop 49 urges a safety plate 44 of the lockout mechanism proximally against the bias of a spring 42. This moves a tab 47 of safety plate 44 (FIG. 6A) out of engagement with the upper surface of the trigger lock 50 (as viewed in the orientation of FIG. 6A) to permit pivoting of trigger lock 50 in the direction of arrow "B" in FIG. 2, thereby unblocking the firing trigger 20 and enabling firing of surgical stapling instrument 10. This is described in detail in the aforementioned U.S. Pat. No. 7,303,106.

As shown in FIGS. 1-4B, approximation indicator mechanism 100 of the present disclosure includes a bulbous approximation indicator 102, lens cover 104 (FIG. 4B) and slide member 110. Indicator 102 is pivotally supported via pin 109 on projecting portion 112 of pivot member 106 which may be formed monolithically with handle assembly 12. Lens cover 104 (or window of handle assembly 12) is positioned above indicator 102 and may be formed of magnification material to facilitate easy visualization of indicator 102. Slide member 110 is slidably positioned within handle assembly 12. A biasing member, e.g., a coil spring 120, is configured to urge slide member 110 distally within stationary handle 18. In the unapproximated (spaced) and unfired position of instrument 10 (FIGS. 1 and 4B), biasing member 120 urges slide member 110 distally to maintain indicator 102 in a first position, which provides indication to a surgeon that the instrument 10 has not been approximated and is not in a fire-ready condition (see FIGS. 1 and 4B). In an alternative embodiment, rather than the indicator attached to pivot member 106 by a pin, projecting portion 112 engages an inner surface of the indicator 102 to maintain the indicator in the first position.

During approximation of anvil assembly 30 and shell assembly 31, a tab 41 of screw stop 49 passes through a slot of slide member 110 and engages a proximal end of the slot. Upon continued approximation of instrument 10, screw 40 (a portion of which being in contact with the proximal end of slot) moves slide member 110 proximally within stationary handle 18 against the bias of spring 120 such that indicator 102 is rotated due to the pin attachment. Approximation indicator 100 pivots (or rotates) to a second position in the same manner as described in U.S. Pat. No. 7,303,106, the entire contents of which was incorporated hereinabove by reference. In an alternative embodiment where the indicator is not pinned, the projecting portion 112 of slide member 110 engages a portion of indicator 102 causing indicator 102 to pivot (or rotate) to a second position. In the second position, indicator 102 provides indication to a surgeon that the instrument has been approximated and is now in a fire-ready position of FIG. 2.

Actuation of firing trigger 20 (i.e., pivoting in the direction of arrow "A" in FIG. 1) causes staples to be ejected from shell assembly 31 towards anvil assembly 30. That is, firing trigger 20 is disposed in mechanical cooperation with a pusher (not explicitly shown in the illustrated embodiments), such that actuation of firing trigger 20 causes advancement of the pusher into contact with the staples to eject the staples into staple deforming pockets of anvil assembly 130. More specifically, when firing trigger 20 is actuated, i.e. pivoted about pivot member 29, firing link 27 (FIG. 4B) is moved proximally. Firing trigger 20 moves distally to advance a pusher link 26 distally against its spring bias. The distal end of pusher link 26, attached to a pusher back (not shown), advances the pusher back to eject the annular rows of staples from the shell assembly 31. Details of the firing mechanism are described in U.S. Pat. No. 7,303,106, incorporated by reference above.

Figure 6:
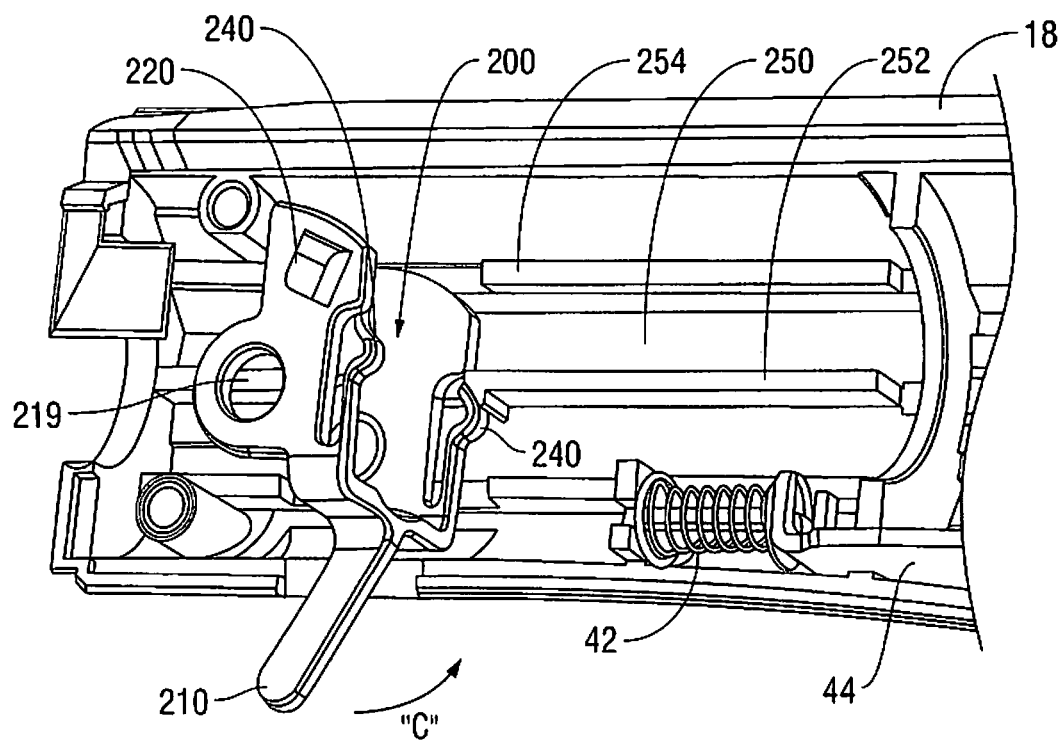
FIG. 6 is a partial cut-away view of the firing indicator within the housing of the surgical stapling instrument.
Figure 6A:
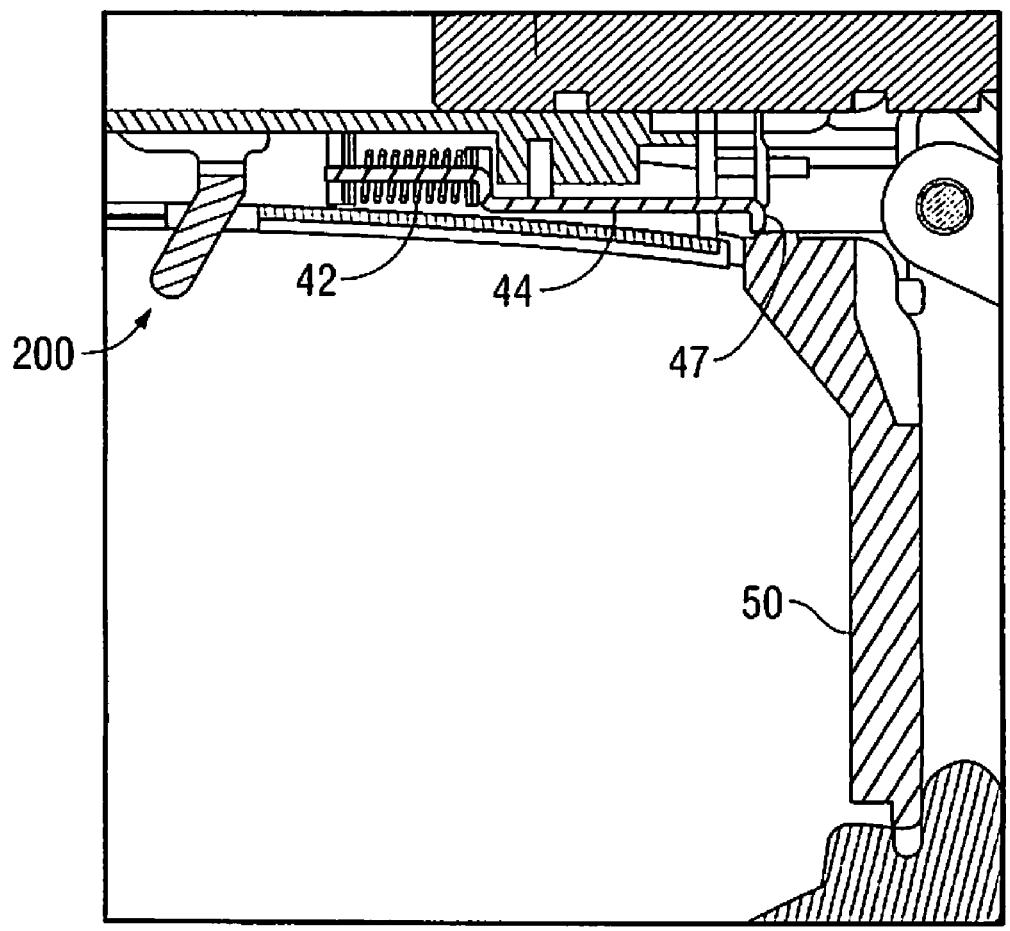
FIG. 6A is a longitudinal cross-sectional view of a portion of the surgical stapling instrument.

Referring now to FIGS. 4B-6, a complete actuation of firing trigger 20 causes firing indicator 200 to pivot (or rotate) (e.g., against an initial bias) from its first position (FIGS. 4B and 4C) to its second position (FIGS. 3 and 5). Specifically, once firing trigger 20 is actuated an engagement structure of firing trigger 20 (e.g., a tab 24 thereon) contacts a portion of firing indicator 200 (e.g., a pawl 210 extending from firing indicator 200 and being monolithically formed therewith or operatively connected thereto). Firing indicator 200 is disposed in mechanical cooperation (e.g., pivotable or rotatable) with stationary handle 18. The engagement between firing trigger 20 and firing indicator 200 (e.g., the engagement between tab 24 and pawl 210 shown in FIG. 5) causes pawl 210 of firing indicator 200 (e.g., pawl 210) to rotate in the general direction of arrow "C" (FIG. 6). The indicator 200 rotates about a pivot point (e.g., a post within stationary handle 18 extending through an opening 219 (FIG. 6) of firing indicator 200. The post is omitted in FIG. 6 for clarity. In the illustrated embodiment, tab 24 includes an angled engagement surface 24a (FIG. 4C) which is angled with respect to a longitudinal axis "A-A" defined by movable handle (firing trigger) 20. Angled engagement surface 24a facilitates the movement of pawl 210 of firing indicator 200 in a distal direction. Note in stapling devices applying annular rows of staples having two movable handles, tab 24 can be positioned on one of the handles.

FIG. 6 illustrates firing indicator 200 in its first position with detents 240, disposed on opposing sides of indicator 200, positioned below ribs 252 (only one of which is shown) in the respective housing half. After firing indicator 200 is moved to its second position of FIG. 3, firing indicator 200 is maintained in its second position by detents 240 engaging a respective recess 250 (only a single recess 250 is shown in FIG. 6 for clarity since the other housing half has been removed) between ribs 252, 254 in each of the body halves. After firing, the firing indicator 200 stays in the second position (i.e., with detents 240 between ribs 252, 254), until a user manually resets the firing indicator 200 to its first position by moving (rotating) a portion of firing indicator 200 (e.g., pawl 210) proximally in the direction opposite arrow C to override the detent 240/recess 250 engagement.

As firing indicator 200 rotates in the direction of arrow C to its second (completed firing) position, indicia 220 (FIG. 6; e.g., color, words, letters, bumps, etc.) thereon is moved from a first position towards a second position. In its second position (i.e., when firing indicator 200 is in its second position, as shown in FIG. 5), indicia 220 is visible to the user, e.g., through a window or opening 230 (FIG. 5) of stationary handle 18. While not explicitly illustrated, it is contemplated that each side of handle assembly 12 includes a lens cover or window thereon. The lens could optionally be made of magnification material. In a preferred embodiment, firing indicator 200 includes a pair of indicia 220 thereon, one on each side, such that each indicia is visible through a corresponding window or opening 230 on each side of the instrument when firing indicator 200 is in its second position.

Figure 4C:
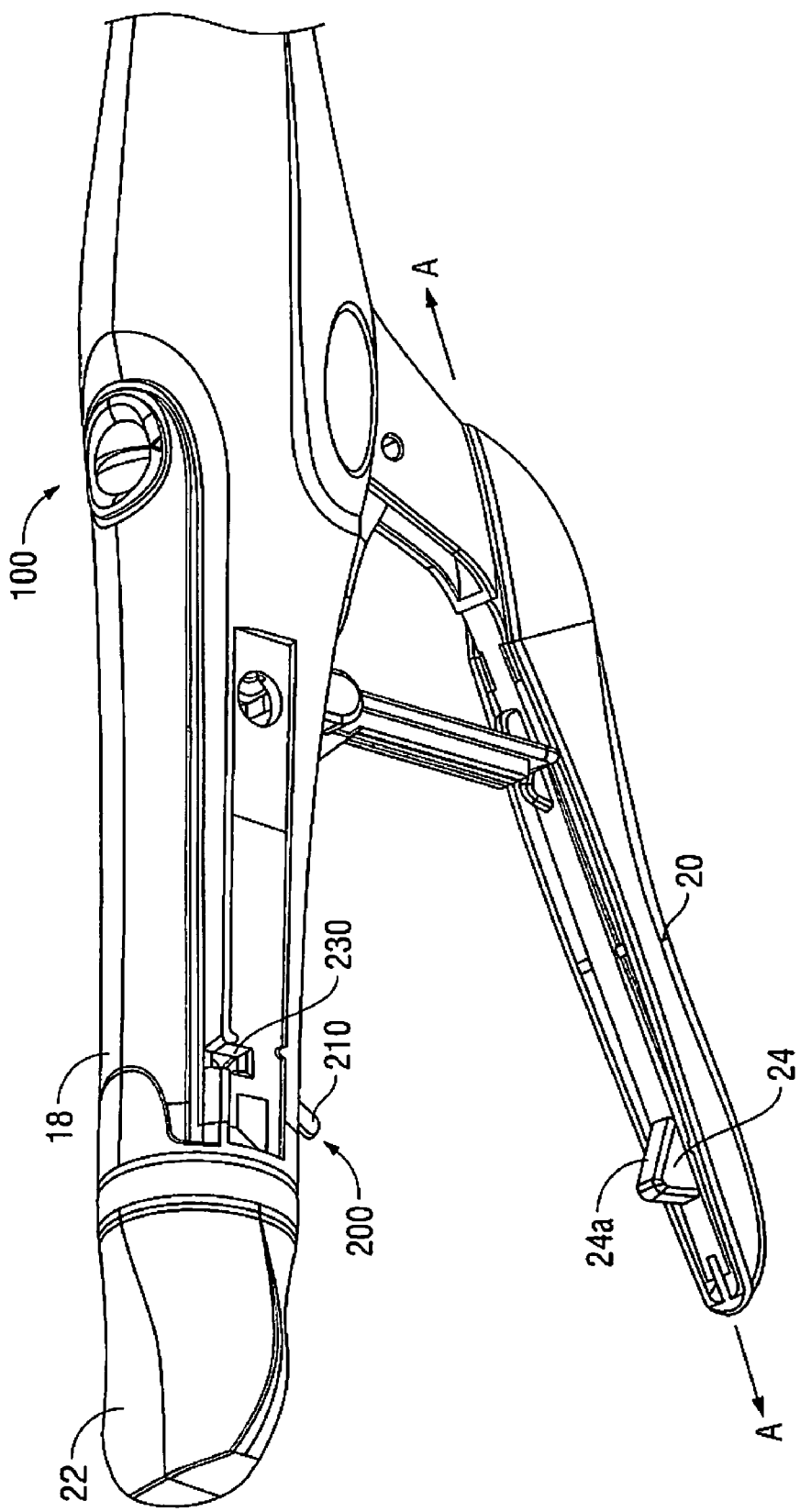
FIG. 4C is a perspective view of the handle assembly of the surgical stapling instrument in the unapproximated position of FIG. 1.

FIG. 4C illustrates firing trigger 20 in an initial pre-fired position, where firing indicator 200 in is first position and where indicia 220 is in its first position not visible through window 230. FIG. 5 illustrates firing trigger 20 in a fired position, where firing indicator 200 is in its second position and wherein indicia 220 is visible through window 230, thus providing an indication to a surgeon that the instrument has been fired.

Further details of other features of surgical instrument 10, such as the approximation assembly, firing assembly, lock out mechanism and approximation indicator mechanism are disclosed in U.S. Pat. Nos. 7,168,604 and 7,303,106, the entire contents of each of which are incorporated by reference herein.

The present disclosure also relates to a method of performing a surgical procedure. The method includes providing a surgical instrument 10 including handle assembly 12, elongated body portion 14 and head portion 16. Handle assembly 12 includes a, firing trigger 20 and firing indicator 200. Elongated body portion 14 extends distally from handle assembly 12. Head portion 16 is disposed adjacent a distal portion of elongated body portion 14 and includes anvil assembly 30 and shell assembly 31. The method also includes positioning surgical instrument 10 adjacent a surgical site and moving firing trigger 20 (preferably relative to stationary handle 18) between a first non-actuated position and a second actuated position such that a portion of firing trigger 20 makes initial contact with a portion of firing indicator 200 (e.g., pawl 210) when firing trigger 20 is moved to its second actuated position. Firing indicator 200 moves from a first position towards a second position upon contact between firing trigger 20 and firing indicator 200.

It will be understood that various modifications may be made to the embodiments disclosed herein. Therefore, the above description should not be construed as limiting, but merely as exemplifications of disclosed embodiments. Those skilled in the art will envision other modifications within the scope and spirit of the claims appended hereto.

What is claimed is:
1. A surgical stapling instrument, comprising:
  a handle assembly including a firing trigger and a firing indicator, the firing trigger being movable between a first non-actuated position and a second actuated position, the firing trigger including engagement structure extending from a proximal region of the firing trigger;
  an elongated body portion extending distally from the handle assembly;

a head portion disposed adjacent a distal portion of the elongated body portion and including an anvil assembly and a shell assembly, the anvil assembly being movable in relation to the shell assembly between spaced and approximated positions;

an approximation mechanism for moving the anvil assembly between spaced and approximated positions; and a firing mechanism for firing fasteners from the shell assembly, wherein the firing indicator is movable independent of movement of the approximation mechanism, and the engagement structure of the firing trigger moves the firing indicator from a first position to a second position when the firing trigger is moved from its first non-actuated position toward its second actuated position.

2. The surgical stapling instrument of claim 1, wherein the handle assembly includes a stationary handle and the firing indicator is rotatable with respect to the stationary handle.

3. The surgical stapling instrument of claim 1, wherein the handle assembly includes a stationary handle and the engagement structure includes a tab, the tab extending towards the stationary handle and is configured to make initial contact with the firing indicator when the firing trigger is moved to its second actuated position.

4. The surgical stapling instrument of claim 3, wherein a surface of the tab is angled with respect to a longitudinal axis defined by the firing trigger.

5. The surgical stapling instrument of claim 1, wherein the firing indicator includes firing indicia thereon and wherein the indicia is visible to a user when the firing indicator is in its second position.

6. The surgical stapling instrument of claim 1, wherein the handle assembly includes a window which enables a user to view a portion of the firing indicator.

7. The surgical stapling instrument of claim 1, wherein the firing indicator is configured to remain in its second position after the firing trigger has been moved to its second actuated position.

8. The surgical stapling instrument of claim 7, wherein the firing indicator includes a detent positionable in a recess in the handle assembly to maintain the firing indicator in the second position.

9. The surgical stapling instrument of claim 8, wherein the firing indicator is reset by manual rotation of the firing indicator in a proximal direction to override the detent.

10. The surgical stapling instrument of claim 1, wherein the firing indicator is configured to move from its first position towards its second position in response to a single actuation stroke of the firing trigger.

11. The surgical stapling instrument of claim 1, further comprising an approximation indicator to indicate the stapling instrument is in a fire-ready position.

12. The surgical stapling instrument of claim 11, wherein the approximation indicator provides visual indication to a user of the device.

13. A surgical stapling instrument, comprising:

a handle assembly including a firing trigger, the firing trigger being movable between a first non-actuated position and a second actuated position;

an elongated body portion extending distally from the handle assembly;

a head portion disposed adjacent a distal portion of the elongated body portion and including an anvil assembly and a shell assembly, the anvil assembly being movable in relation to the shell assembly between spaced and approximated positions;

an approximation indicator disposed in mechanical cooperation with the handle assembly, the approximation indicator being configured to move from a first position towards a second position in response to the anvil assembly moving in relation to the shell assembly towards its approximated position; and a firing indicator disposed in mechanical cooperation with the handle assembly and independent from the approximation indicator and independent of movement of the anvil assembly toward the approximation position, the firing indicator being configured to move from a first position towards a second position in response to the firing trigger moving towards its second actuated position.

14. The surgical stapling instrument of claim 13, wherein the firing indicator is configured to move from its first position towards its second position in response to a single actuation stroke of the firing trigger.

15. The surgical stapling instrument of claim 13, wherein the firing indicator is maintained in the second position until manually released.

16. The surgical stapling instrument of claim 13, wherein the handle assembly includes a stationary handle and the firing indicator is rotatable with respect to the stationary handle.

17. The surgical stapling instrument of claim 13, wherein the approximation indicator provides visual indication to a user of the device.

* * * * *